(12) United States Patent
Moore et al.

(10) Patent No.: US 10,429,184 B2
(45) Date of Patent: Oct. 1, 2019

(54) ENVIRONMENTAL MONITORING SYSTEM INCLUDING AN UNDERWATER SENSOR ASSEMBLY

(71) Applicant: Aridea LLC, Charleston, WV (US)

(72) Inventors: Robert E. Moore, Clendenin, WV (US); Jason J. Martin, Charleston, WV (US)

(73) Assignee: Aridea LLC, Charleston, WV (US)

( * ) Notice: Subject to any disclaimer, the term of this patent is extended or adjusted under 35 U.S.C. 154(b) by 266 days.

(21) Appl. No.: 15/480,742

(22) Filed: Apr. 6, 2017

(65) Prior Publication Data

US 2018/0292208 A1 Oct. 11, 2018

(51) Int. Cl.
*E02D 1/02* (2006.01)
*G01C 13/00* (2006.01)
*G01N 33/18* (2006.01)

(52) U.S. Cl.
CPC ....... *G01C 13/008* (2013.01); *G01N 33/1886* (2013.01)

(58) Field of Classification Search
CPC .. G01C 13/008; G01C 13/002; G01C 13/004; G01C 13/006; G01C 13/00; G01C 15/00; G01N 33/1886; E02D 1/025; E21B 7/185; E21B 25/18; B60R 16/0237; F42B 15/08; G08G 5/0091
See application file for complete search history.

(56) References Cited

U.S. PATENT DOCUMENTS

| | | | | |
|---|---|---|---|---|
| 5,231,252 A * | 7/1993 | Sansone | ................... | G01V 1/16 181/112 |
| 6,119,630 A * | 9/2000 | Lobsiger | ............ | G01N 33/1886 119/238 |
| 8,758,072 B2 * | 6/2014 | Voisin | ..................... | B63B 21/66 441/1 |
| 2015/0117148 A1* | 4/2015 | Drange | ................ | G01C 21/165 367/19 |
| 2015/0377852 A1* | 12/2015 | Hartland | .............. | G01V 1/3817 73/170.33 |
| 2016/0018377 A1* | 1/2016 | Corbett | .............. | G01N 33/1886 414/137.9 |

* cited by examiner

*Primary Examiner* — Harshad R Patel
*Assistant Examiner* — Nigel H Plumb
(74) *Attorney, Agent, or Firm* — The Webb Law Firm (57) ABSTRACT

An underwater sensor assembly includes a frame configured to sit on a bottom of a body of water and at least one first sensor connected to the frame. The at least one first sensor is configured to measure at least one parameter related to the body of water. A system for environmental monitoring includes the underwater sensor assembly, at least one buoy at a surface of the body of water, and at least one cable attached at a first end to the frame and attached at a second end opposite the first end to the at least one buoy. The at least one buoy comprises at least one second sensor configured to measure at least one parameter above the surface of the body of water.

22 Claims, 3 Drawing Sheets

ENVIRONMENTAL MONITORING SYSTEM INCLUDING AN UNDERWATER SENSOR ASSEMBLY

BACKGROUND

Field

Disclosed embodiments relate generally to environmental monitoring and, more particularly, to an underwater sensor assembly and a system for environmental monitoring of bodies of water.

Description of Related Art

Environmental monitoring presents various challenges including constantly changing and/or harsh environmental conditions and remote locations. Water is one of the most precious commodities on earth. It is vital to health, communities, and the environment. Monitoring of a body of water, such as a river, a stream, a lake, a sea, a pond, etc., poses particular challenges, such as stabilizing and/or positioning sensors in the body or water, reliably collecting and transmitting data from the sensors, and powering the sensors.

For example, rivers are home to populations of various species of mussels that even most locals know very little about; however, that does not mean that these mussels are of little importance to the overall ecosystem. Freshwater mussels are not only an important food source for muskrats, waterfowl and fish, but are also very important indicators of water quality. Because of the vital role that these bi-valves play in the ecosystem, it is imperative to protect them when working in local rivers and streams. Navigable locks on rivers require dredging operations to keep the navigation channels open and operable. The effects of dredging on the local mussel populations should be monitored to ensure the health of the mussels, as well as that of the overall ecosystem.

Further, by monitoring various characteristics of bodies of water, state and federal agencies can be assured that no dangerous contaminants are reaching public watersheds. By conducting this monitoring at regular intervals, the reduction of potential contaminates can be controlled and optimized.

Accordingly, there is a need in the art for an improved underwater sensor assembly and system for environmental monitoring of bodies of water.

SUMMARY

Provided is an underwater sensor assembly and system for environmental monitoring of bodies of water.

According to one preferred and non-limiting embodiment or aspect, provided is an underwater sensor assembly, comprising: a frame configured to sit on a bottom of a body of water; and at least one first sensor connected to the frame, wherein the at least one first sensor is configured to measure at least one parameter related to the body of water.

In one preferred and non-limiting embodiment or aspect, the frame comprises a plurality of legs connected to a mount, wherein the plurality of legs are configured to allow water to flow between the plurality of legs.

In one preferred and non-limiting embodiment or aspect, at least one leg of the plurality of legs comprises a substantially circular base at a first end, and wherein the at least one leg is connected to the mount at a second end opposite the first end.

In one preferred and non-limiting embodiment or aspect, the circular base comprises a traction mechanism on a face of the base facing away from the mount.

In one preferred and non-limiting embodiment or aspect, the at least one first sensor is configured to measure a distance from the at least one first sensor to the bottom of the body of water.

In one preferred and non-limiting embodiment or aspect, the at least one first sensor is further configured to determine a composition of sediment at the bottom of the body of water.

In one preferred and non-limiting embodiment or aspect, the underwater sensor assembly further comprises at least one cable attached at a first end to the frame and extending toward a surface of the body of water.

In one preferred and non-limiting embodiment or aspect, the underwater sensor assembly further comprises at least one second sensor connected to the at least one cable between the frame and the surface of the body of water.

In one preferred and non-limiting embodiment or aspect, the at least one second sensor is configured to measure at least one of temperature, conductivity, depth, pH, turbidity, dissolved oxygen saturation, and dissolved oxygen.

In one preferred and non-limiting embodiment or aspect, the at least one second sensor comprises a plurality of second sensors connected to the at least one cable between the frame and the surface of the body of water, and wherein the plurality of second sensors are spaced apart from each other along the cable between the frame and the surface of the body of water.

In one preferred and non-limiting embodiment or aspect, two or more sensors of the plurality of second sensors are configured to measure a same parameter, and wherein the two or more sensors of the plurality of second sensors measure the same parameter at different depths in the body of water.

In one preferred and non-limiting embodiment or aspect, the at least one cable is attached at a second end to at least one buoy at the surface of the body of the water.

In one preferred and non-limiting embodiment or aspect, the at least one cable comprises at least one data line configured to carry data from the at least one first sensor to control circuitry on the at least one buoy.

In one preferred and non-limiting embodiment or aspect, the at least one buoy comprises a transmitter in communication with the control circuitry and configured to wirelessly transmit the data to at least one computer located outside the body of water.

In one preferred and non-limiting embodiment or aspect, the control circuitry is configured to determine a level of sediment at the bottom of the body of water based on the distance from the at least one first sensor to the bottom of the body of water In one preferred and non-limiting embodiment or aspect, the control circuitry is configured to transmit an alert to the at least one computer when the level of sediment violates a threshold level.

In one preferred and non-limiting embodiment or aspect, the at least one buoy comprises at least one third sensor configured to measure at least one weather related parameter, at least one air quality parameter, at least one wave related parameter, or any combination thereof.

In one preferred and non-limiting embodiment or aspect, the at least one first sensor comprises at least one ultrasonic transducer.

In one preferred and non-limiting embodiment or aspect, the at least one first sensor comprises a plurality of sensors, and wherein the plurality of sensors are located at different distances from the bottom of the body of water when the frame sits on the bottom of the body of water.

In one preferred and non-limiting embodiment or aspect, the at least one first sensor comprises a plurality of sensors, and wherein the plurality of sensors are located at substantially a same distance from the bottom of the body of water when the frame sits on the bottom of the body of water.

In one preferred and non-limiting embodiment or aspect, the frame comprises a simple polygonal shape with a leg extending from each corner of the simple polygonal shaped frame.

In one preferred and non-limiting embodiment or aspect, each of the legs extends from the simple polygonal shaped frame in a direction away from the interior of the simple polygonal shaped frame.

According to one preferred and non-limiting embodiment or aspect, provided is a system for environmental monitoring, comprising: an underwater sensor assembly including: a frame configured to sit on a bottom of a body of water, at least one first sensor connected to the frame, wherein the at least one first sensor is configured to measure at least one parameter below the surface of the body of water; at least one buoy at a surface of the body of water; and at least one cable attached at a first end to the frame and attached at a second end opposite the first end to the at least one buoy, wherein the at least one buoy comprises at least one second sensor configured to measure at least one parameter above the surface of the body of water.

In one preferred and non-limiting embodiment or aspect, the system further comprises at least one third sensor connected to the at least one cable between the frame and the surface of the body of water.

Other preferred and non-limiting embodiment or aspects of the present invention will be set forth in the following numbered clauses:

Clause 1. An underwater sensor assembly, comprising: a frame configured to sit on a bottom of a body of water; and at least one first sensor connected to the frame, wherein the at least one first sensor is configured to measure at least one parameter related to the body of water.

Clause 2. The underwater sensor assembly of clause 1, wherein the frame comprises a plurality of legs connected to a mount, wherein the plurality of legs are configured to allow water to flow between the plurality of legs.

Clause 3. The underwater sensor assembly of clause 1 or 2, wherein at least one leg of the plurality of legs comprises a substantially circular base at a first end, and wherein the at least one leg is connected to the mount at a second end opposite the first end.

Clause 4. The underwater sensor assembly of any of clauses 1-3, wherein the circular base comprises a traction mechanism on a face of the base facing away from the mount.

Clause 5. The underwater sensor assembly of any of clauses 1-4, wherein the at least one first sensor is configured to measure a distance from the at least one first sensor to the bottom of the body of water.

Clause 6. The underwater sensor assembly of any of clauses 1-5, wherein the at least one first sensor is further configured to determine a composition of sediment at the bottom of the body of water.

Clause 7. The underwater sensor assembly of any of clauses 1-6, further comprising: at least one cable attached at a first end to the frame and extending toward a surface of the body of water.

Clause 8. The underwater sensor assembly of any of clauses 1-7, further comprising: at least one second sensor connected to the at least one cable between the frame and the surface of the body of water.

Clause 9. The underwater sensor assembly of any of clauses 1-9, wherein the at least one second sensor is configured to measure at least one of temperature, conductivity, depth, pH, turbidity, dissolved oxygen saturation, and dissolved oxygen.

Clause 10. The underwater sensor assembly of any of clauses 1-10, wherein the at least one second sensor comprises a plurality of second sensors connected to the at least one cable between the frame and the surface of the body of water, and wherein the plurality of second sensors are spaced apart from each other along the cable between the frame and the surface of the body of water.

Clause 11. The underwater sensor assembly of any of clauses 1-11, wherein two or more sensors of the plurality of second sensors are configured to measure a same parameter, and wherein the two or more sensors of the plurality of second sensors measure the same parameter at different depths in the body of water.

Clause 12. The underwater sensor assembly of any of clauses 1-11, wherein the at least one cable is attached at a second end to at least one buoy at the surface of the body of the water.

Clause 13. The underwater sensor assembly of any of clauses 1-12, wherein the at least one cable comprises at least one data line configured to carry data from the at least one first sensor to control circuitry on the at least one buoy.

Clause 14. The underwater sensor assembly of any of clauses 1-13, wherein the at least one buoy comprises a transmitter in communication with the control circuitry and configured to wirelessly transmit the data to at least one computer located outside the body of water.

Clause 15. The underwater sensor assembly of any of clauses 1-14, wherein the control circuitry is configured to determine a level of sediment at the bottom of the body of water based on the distance from the at least one first sensor to the bottom of the body of water Clause 16. The underwater sensor assembly of any of clauses 1-15, wherein the control circuitry is configured to transmit an alert to the at least one computer when the level of sediment violates a threshold level.

Clause 17. The underwater sensor assembly of any of clauses 1-16, wherein the at least one buoy comprises at least one third sensor configured to measure at least one weather related parameter, at least one air quality parameter, at least one wave related parameter, or any combination thereof.

Clause 18. The underwater sensor assembly of any of clauses 1-17, wherein the at least one first sensor comprises at least one ultrasonic transducer.

Clause 19. The underwater sensor assembly of any of clauses 1-18, wherein the at least one first sensor comprises a plurality of sensors, and wherein the plurality of sensors are located at different distances from the bottom of the body of water when the frame sits on the bottom of the body of water.

Clause 20. The underwater sensor assembly of any of clauses 1-19, wherein the at least one first sensor comprises a plurality of sensors, and wherein the plurality of sensors are located at substantially a same distance from the bottom of the body of water when the frame sits on the bottom of the body of water.

Clause 21. The underwater sensor assembly of any of clauses 1-20, wherein the frame comprises a simple polygonal shape with a leg extending from each corner of the simple polygonal shaped frame.

Clause 22. The underwater sensor assembly of any of clauses 1-21, wherein each of the legs extends from the simple polygonal shaped frame in a direction away from the interior of the simple polygonal shaped frame.

Clause 23. A system for environmental monitoring, comprising: an underwater sensor assembly including: a frame configured to sit on a bottom of a body of water, and at least one first sensor connected to the frame, wherein the at least one first sensor is configured to measure at least one parameter below the surface of the body of water; at least one buoy at a surface of the body of water; and at least one cable attached at a first end to the frame and attached at a second end opposite the first end to the at least one buoy, wherein the at least one buoy comprises at least one second sensor configured to measure at least one parameter above the surface of the body of water.

Clause 24. The system of clause 23, further comprising: at least one third sensor connected to the at least one cable between the frame and the surface of the body of water.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 1:
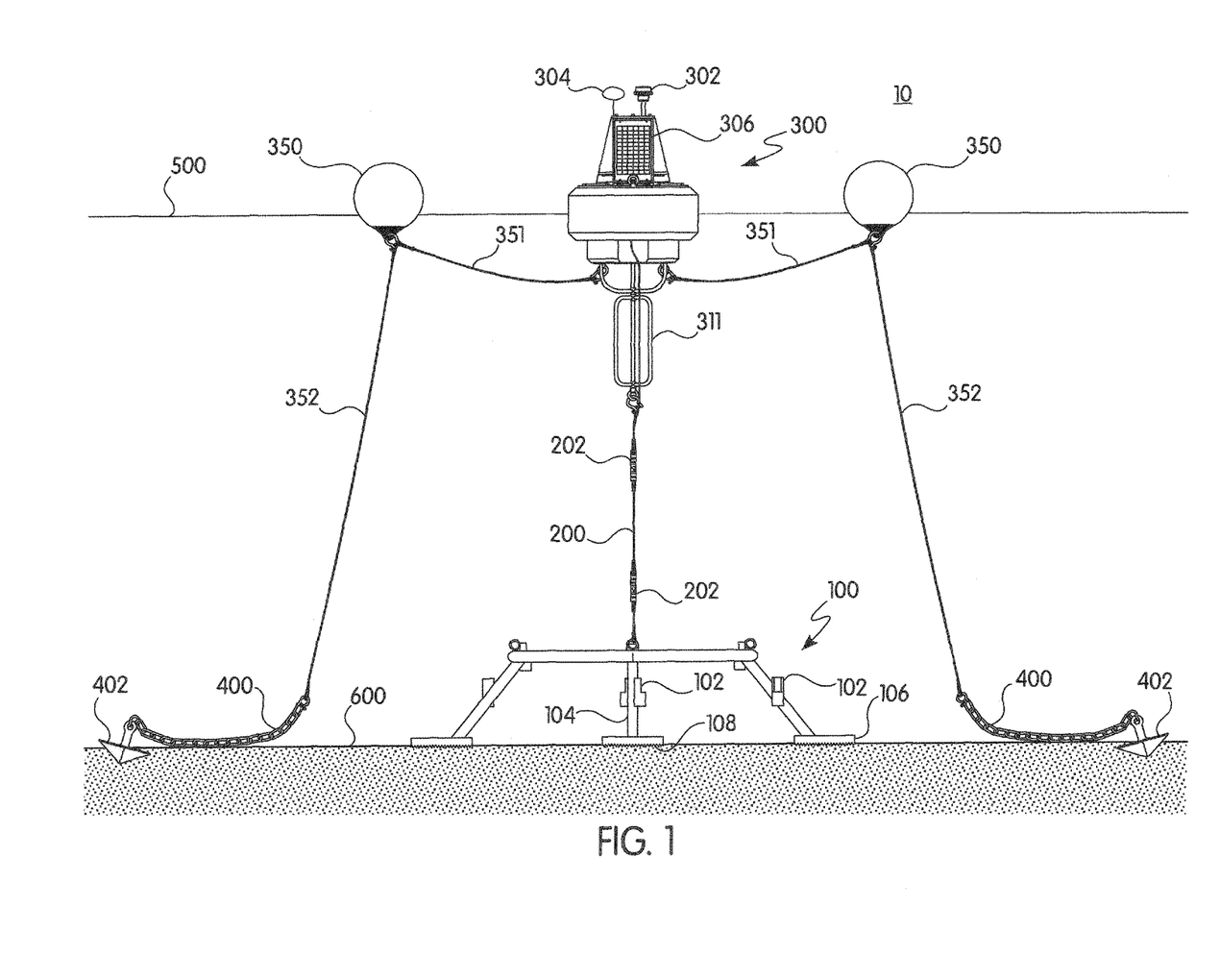
FIG. 1 is a schematic diagram of a system for environmental monitoring according to preferred and non-limiting embodiments or aspects.

Referring to FIG. 1, a system for environmental monitoring 10 according to preferred and non-limiting embodiments or aspects comprises an underwater sensor assembly 100 at a bottom of a body of water 600 and at least one buoy 300 at a surface of the body of water 500. The underwater sensor assembly 100 includes a frame 101 configured to sit on the bottom of the body of water 600 and at least one first sensor 102 connected to the frame 101. The at least one first sensor 102 can be configured to measure at least one parameter related to the body of water and/or below the surface of the body of water 500. At least one cable 200 is attached at a first end to the frame 101 and attached at a second end opposite the first end to the at least one buoy 300. At least one second sensor 202 may be connected to the at least one cable 200 between the frame 101 and the surface of the body of water 500. The at least one second sensor 202 can be configured to measure at least one parameter related to the body of water and/or below the surface of the body of water 500. The at least one buoy 300 may include at least one third sensor 302 configured to measure at least one parameter at or above the surface of the body of water 500.

The at least one buoy 300 may be connected to marker buoys 350, which are at the surface of the water 500, via marker lines 351. The marker buoys 350 are connected via mooring lines 352 to chains 400, and the chains 400 are connected to anchors 402 that rest on the bottom of the body of water. The marker buoys 350 and anchors 402 help to secure and stabilize the at least one buoy 300 at a desired location in the body of water, as well as provide visible markers to indicate the presence of the at least one buoy 300 and the underwater sensor assembly 100 in the body of water.

Figure 2:
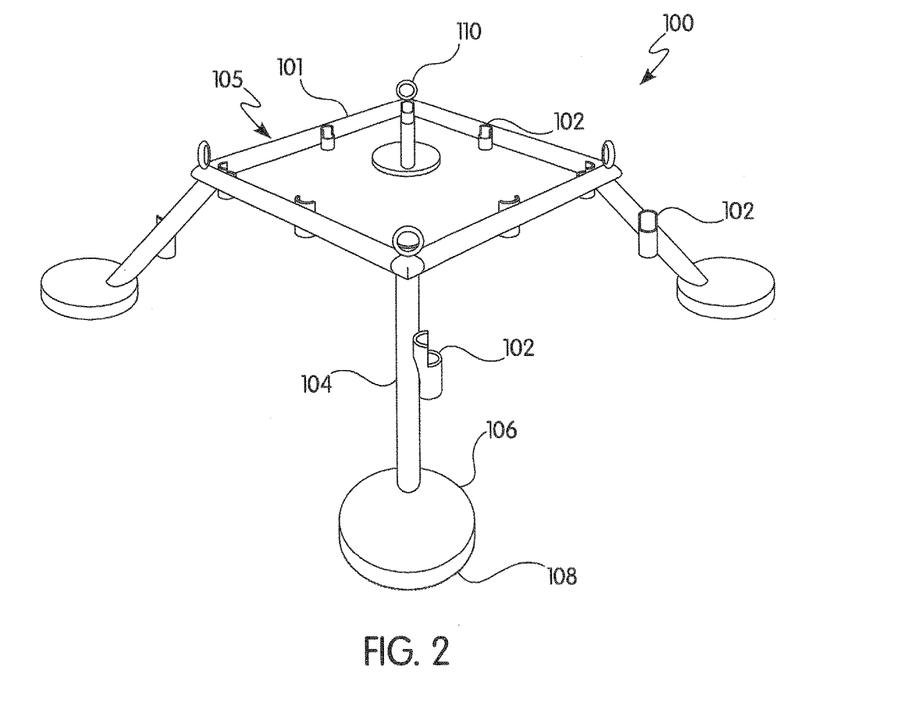
FIG. 2 is a perspective view of an underwater sensor assembly according to preferred and non-limiting embodiments or aspects.

Referring now to FIG. 2, the frame 101 of the underwater sensor assembly 100 comprises a plurality of legs 104 connected to a mount 105. The mount 105 may be open between sides thereof to allow water to flow through the mount 105, for example, as shown in FIG. 2. The plurality of legs 104 are configured to allow water to flow between the legs 104. At least one leg of the plurality of legs 104 may comprise a base 106 at a first end, and the at least one leg may be connected to the mount 105 at a second end opposite the first end. The base 106 can include a traction mechanism 108, such as spikes, treading, and/or felt, on a face of the base 106 facing away from the mount 105 that directly contacts the bottom of the body of water 600. In one example, the base 106 has a substantially circular shape, as shown in FIG. 2, which can reduce the creation of eddies caused by currents in the water flowing over the base 106. Eddies can increase localized sediment buildup at the bottom of the body of water 600.

The underwater sensor assembly 100 can be connected to the at least one cable 200 at one or more mounting points 110, such as a ring as shown in FIG. 2. In one implementation, the at least one cable 200 may comprise a chain (not shown) similar to the chains 400 at the end thereof that connects to the underwater sensor assembly. In one example, the at least one cable 200 may split into multiple cables, with ends of the multiple cables connected to each of a plurality of mounting points 110 of the underwater sensor assembly 100 to provide a center mount such that the underwater sensor assembly 100 can be lowered to the bottom of the body of water 600 in a manner in which each of the bases 106 contact the bottom of the body of water 600 at substantially the same time. In another example, the at least one cable 200 may be connected to only one or less than all of the mounting points 110 to provide a side mount such that the underwater sensor assembly can be lowered to the bottom of the body of water 600 in a manner in which only one base 106 or only a portion of the plurality of bases 106 contact the bottom of the body of water 600 before the remainder of the bases of the plurality of bases 106. A side mount may enable easier and/or more adroit maneuvering of the underwater sensor assembly 100 during deployment, which can help to ensure a more stable and/or level placement of the underwater sensor assembly 100 on the bottom of the body of water 600. The underwater sensor assembly 100 can be deployed without divers with deployment thereof controlled from the surface of the body of water 500 by lowering the underwater sensor assembly via the at least one cable 200 to the bottom of the body of water 600 and adjusting the placement via the at least one cable 200.

In one example, the at least one first sensor 102 is configured to measure a distance from the at least one first sensor 102 to the bottom of the body of water 600, e.g., an open substrate depth below the sensor 102 to measure natural sediment deposition and scour below the underwater sensor assembly 100. For example, the at least one first sensor 102 may comprise at least one ultrasonic transducer, such as the SeaTek Ultrasonic Ranging System by Seatek, which can measure changes in sediment of 1 millimeter. The at least one first sensor 102 is connected to the frame 101 and angled to face the bottom of the body of water 600 when the underwater sensor assembly 100 sits on the bottom of the body of water 600. In some examples, the at least one first sensor 102 can be configured to determine a composition of sediment at the bottom of the body of water 600. In another example, the at least one first sensor 102 can be configured to determine at least one of temperature, conductivity, depth, pH, turbidity, dissolved oxygen saturation, and dissolved oxygen. In one implementation, the at least one first sensor 102 can include a YSI multi-parameter data sonde by YSI Inc. or Xylem Inc. In some implementations, the at least one first sensor 102 can be remotely adjustable via a wired (e.g., the at least one cable 200), or a wireless connection to change the angle and/or placement of the sensor and/or, the type(s) of measurements taken by the sensor, and/or a frequency of the measurements.

The at least one first sensor 102 can include a plurality of first sensors 102. In one example, the plurality of first sensors 102 may be located at different distances from the bottom of the body of water 600 when the frame 101 sits on the bottom of the body of water 600. For example, as shown in FIG. 2, sensors 102 connected to the legs 104 are located a shorter distance from the bottom of the body of water 600 than sensors 102 connected to the mount 105. In another example, the plurality of sensors 102 may be located at substantially a same distance from the bottom of the body of water when the frame 101 sits on the bottom of the body of water. For example, the underwater sensor assembly 100 may comprise only sensors 102 connected to the legs 104 (or vice versa the mount 105). Each of the plurality of first sensors 102 may be configured to measure the distance to the bottom of the body of water 600, a composition of sediment at the bottom of the body water 600, temperature, conductivity, depth, pH, turbidity, dissolved oxygen saturation, dissolved oxygen, or any combination thereof.

In one example, the frame 101 comprises a simple polygonal shape with a leg extending from each corner of the simple polygonal shaped frame. For example, the mount 105 may have a square shape as shown in FIG. 2 with four legs 104 extending from the corners of the square shaped mount 105. The frame 101 may comprise aluminum and/or stainless steel tubing. The aluminum and/or stainless steel tubing may be filled with lead, concrete, or another heavy material to increase the stability of the frame 101. The first sensors 102 may located in sensor mounts, such as stainless steel cut outs or mounts, in or on the frame 101, for example, as shown in FIG. 2, such that the sensors can be screwed and/or taped to the frame 101 for added security. However, it is noted that the shape of the frame is not limited to polygonal shapes and the frame may have any shape with a plurality of legs 104 extending therefrom. For example, the mount 105 may include a circular shape with three or more legs 104 extending therefrom. Each of the legs 104 may extend from the frame 101 in a direction away from the interior of the mount 105. For example, as shown in FIG. 2, the legs 104 extend outwards from the interior of the square shaped mount 105, which can reduce the creation of eddies caused by currents in the water flowing over the legs 104.

Referring again to FIG. 1, the at least one second sensor 202 connected to the at least one cable between the frame and the surface of the body of water can be configured to measure at least one of temperature, conductivity, depth, pH, turbidity, dissolved oxygen saturation, and dissolved oxygen. In one example, the at least one second sensor 202 comprises a plurality of second sensors 202 connected to the at least one cable between the frame 101 and the surface of the body of water 500 (or the buoy 300). The plurality of second sensors 202 can be spaced apart from each other along the cable 200 between the frame 101 and the surface of the body of water 500 (or the buoy 300). Two or more sensors of the plurality of second sensors 202 may be configured to measure a same parameter at different depths in the body of water. For example, dissolved oxygen saturation and/or dissolved oxygen may be different at deeper depths of the body of water where the water has a lower temperature than at depths closer to the surface of the body of water 500 where the water is warmer. The plurality of second sensors 202 can determine and differentiate between various water quality parameters at different depths in the same body of water.

The at least one cable 200 comprises at least one data line configured to connect to and carry data from the at least one first sensor 102 and/or the at least one second sensor 202 to control circuitry 301 (FIG. 4) on the at least one buoy 300. In some implementations, the at least one cable 200 can also provide power to the sensors 102 and 202. In other implementations, the sensors 102 and 202 can be battery powered. The data line may run within the interior of the at least one cable 200, which may comprise a waterproof exterior sheath and connections with the sensors 102, 202, and/or 302. In some implementations, the interior of the at least one cable may comprise a plurality of data and/or power lines. In another example, the at least one first sensor 102, the at least one second sensor 202, and/or the at least one third sensor 302 can be configured to wirelessly transmit sensed data to the transceiver 304/control circuitry 301 and/or directly to a remote computer or at least one computer located outside the body of water, such as an Aridea V2 Gateway by Aridea Solutions. In one implementation, the data is compatible with the Thinginformer Software Platform by Aridea Solutions and/or Microsoft Excel.

In some examples, the at least one cable 200 may be connected to the at least one buoy 300 via an instrument cage 311. The instrument cage 311 can be connected between or along the at least on cable 200 and a bottom of the at least on buoy 300 and be configured to hold one or more of the at least one second sensors 202. In another example, the at least one cable 200 is connected directly to the at least one buoy 300.

Figure 3:
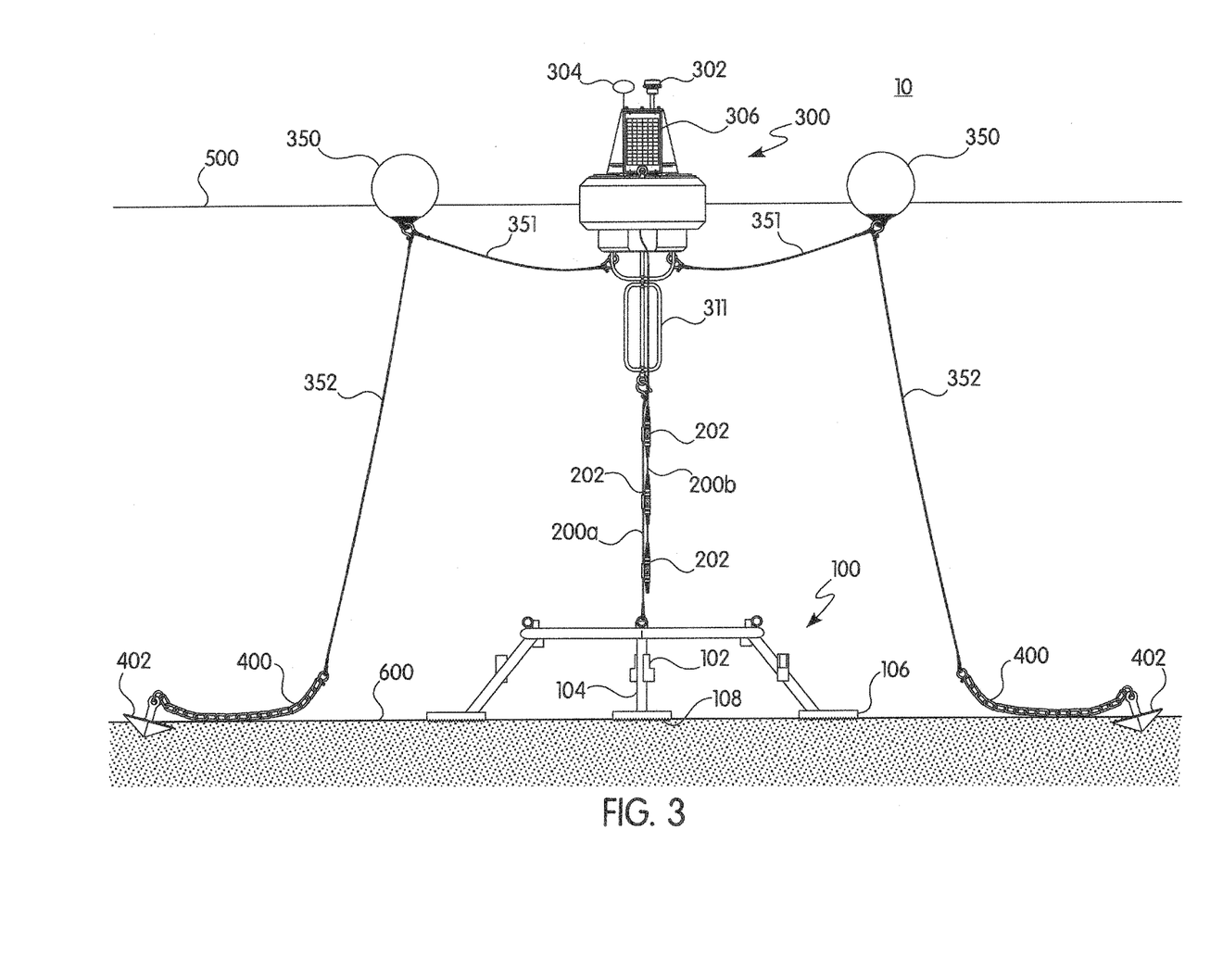
FIG. 3 is a schematic diagram of a system for environmental monitoring according to preferred and non-limiting embodiments or aspects.

In another example, referring to FIG. 3, the at least one cable 200 can comprise a plurality of cables 200a, 200b, etc. The at least one first sensor 102 may be connected to a first cable 200a and the at least one second sensor 202 may be connected to a second cable 200b. Alternatively, a first cable 200a may comprise only a structural cable connecting the underwater sensor assembly 100 to the buoy 300 and a second cable 200b may be connected to the first and second sensors 102 and 202 to communicate the data therefrom to the control circuitry 301.

Figure 4:
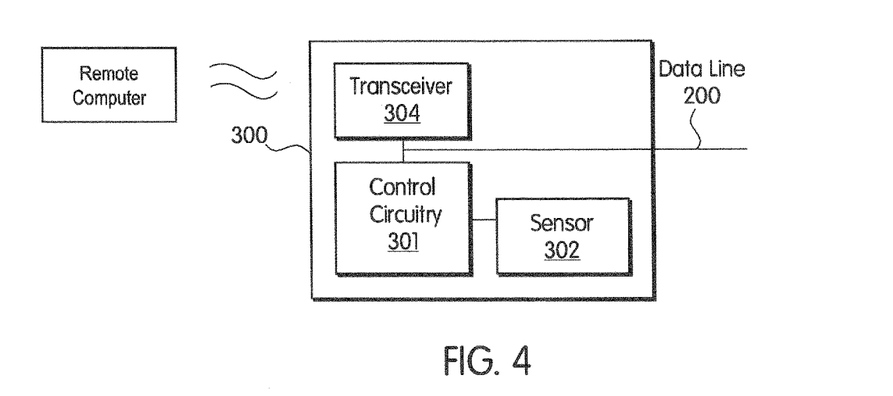
FIG. 4 is a block diagram of a buoy according to preferred and non-limiting embodiments or aspects.

Referring now to FIGS. 1, 3, and 4, the at least one buoy 300 comprises a transceiver 304 in communication with the control circuitry 301 and configured to wirelessly transmit data from the at least one first sensor 102, the at least one second sensor 202, the at least one third sensor 302, and/or the control circuitry 301 to a remote computer or at least one computer located outside the body of water. The at least one third sensor 302 can be configured to measure one or more parameters related to weather, such as air temperature, atmospheric (barometric) pressure, humidity, precipitation, solar radiation and wind, one or more parameters related to air quality, such as Suspended Particulate Matter (SPM), Respirable Suspended Particulate Matter (RSPM), Sulphur dioxide ($SO_2$), Oxides of Nitrogen (NOx), Carbon Monoxide (CO), oxygen, one or more parameters related to wave movement at the surface of the body of water 500, such as water level, temperature, tides, wave action, or tilt action, or any combination thereof.

The at least one buoy 300 can be powered by a battery (not shown) and/or a solar panel 306 configured to charge the battery and/or provide power directly to the control circuitry 301, the at least one third sensor 302, the transceiver 304, and any other electrical components on the buoy 300. In one implementation, the at least one buoy 300 can include a NexSens CB-450 Data Buoy manufactured by NexSens Technology, Inc.

In one example, the control circuitry 301 is configured to determine a level of one or more of the parameters measured by the first sensor(s) 102, second sensor(s) 202, and/or third sensor(s) 302. The control circuitry 301 may be configured to transmit an alert to the remote computer or at least one computer located outside the body of water, such as an Aridea V2 Gateway by Aridea Solutions, when the level of the one or more parameters violates a threshold level associated with the one or more parameters. For example, the control circuitry 301 can be configured to determine a level of sediment at the bottom of the body of water 600 based on the distance from the at least one first sensor 102 to the bottom of the body of water 600. The control circuitry 301 can compare a current distance to a distance measured when the underwater sensor assembly 100 was first deployed and/or to a known height of the first sensor 102 to the bottom of the bases 106 that contact the bottom of the body of water 600. The control circuitry 301 may be configured to transmit an alert to the at least one computer when the level of sediment violates a threshold level. The at least one computer may be configured to alert a monitoring user in response to the alert from the control circuitry 301, e.g., by a sending a text, email, or another notification to a mobile device of the monitoring user.

In some examples, the control circuitry 301 may be configured to process measurements of the same parameter from a plurality of different sensors together. For example, the control circuitry 301 may process measurements from a plurality of the first sensors 102, which can be ultrasonic transducers configured to measure the distance to the bottom of the body of water 600, to determine whether a mean, a median, or other statistical calculation of the plurality of measurements violates a threshold level, for example, a threshold level for sediment level at the bottom of the body of water 600. In one example, the control circuitry 301 may be configured to determine whether a number of measurements from the plurality of sensors which sense the same parameter violates a threshold number of measurements. For example, if the underwater sensor assembly includes eight ultrasonic transducers as the first sensors 102 configured to measure the distance to the bottom of the body of water 600, the control circuitry 301 may require at least four of the eight sensors to measure distances that violate the threshold level for a distance to the bottom before determining that the threshold number is violated and issuing an alert to the at least one computer that the sediment level is too high. In another example, threshold levels associated with measured parameters may be different based on the sensor that is measuring the parameter. For example, if the plurality of second sensors 202 are configured to measure the same parameter, e.g., oxygen level, at different depths in the body of water, the second sensor 202 located at the lower depth in the body of water may be associated with a higher threshold for the oxygen level than the second sensor 202 located closer to the surface of the body of water 500.

Although described mainly with respect to the control circuitry 301, the determination of a level of sediment or a level or amount of any parameter measured by the at least one first sensor 102, the at least on second sensor 202, and/or the at least one third sensor 302, the processing thereof, and/or the alerting and notification based thereon may be implemented by, programmed or configured on, or otherwise associated with any type of computer or processor, such as one or more of the following: a specially-programmed computer, a controller in or associated with the sensors 102, 202, 302, the control circuitry 301 on the buoy 300, the at least one remote computer outside the body of water, a remote server, a networked computer, an Aridea V2 Gateway by Aridea Solutions, or any combination thereof. Accordingly, some or all of the steps in the system, process, and method discussed herein may be implemented and/or executed at the underwater sensor assembly 100 and/or the buoy 300, and similarly, some or all of the steps in the system, process, and method discussed hereinafter may be implemented and/or executed by a computer or processor that is remote from the underwater sensor assembly and/or the buoy 300, where the remote computer or processor is in direct or indirect communication with the transceiver 304 of the buoy 300.

Although the invention has been described in detail for the purpose of illustration based on what is currently considered to be the most practical and preferred embodiments or aspects, it is to be understood that such detail is solely for that purpose and that the invention is not limited to the disclosed embodiments or aspects, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An underwater sensor assembly, comprising:
   a frame configured to sit on a bottom of a body of water; and
   at least one first sensor connected to the frame, wherein the at least one first sensor is configured to measure at least one parameter related to the body of water,
   wherein the frame comprises a plurality of legs and a mount, wherein the plurality of legs extend from the mount and are configured to allow water to flow between the plurality of legs, and wherein at least one leg of the plurality of legs comprises a circular base at a first end, and wherein the at least one leg is connected to the mount at a second end opposite the first end.

2. The underwater sensor assembly of claim 1, wherein the circular base comprises a traction mechanism on a face of the base facing away from the mount.

3. The underwater sensor assembly of claim 1, wherein the at least one first sensor is configured to measure a distance from the at least one first sensor to the bottom of the body of water.

4. The underwater sensor assembly of claim 3, wherein the at least one first sensor is further configured to determine a composition of sediment at the bottom of the body of water.

5. The underwater sensor assembly of claim 1, further comprising:
at least one cable attached at a first end to the frame and extending toward a surface of the body of water.

6. The underwater sensor assembly of claim 1, wherein the at least one first sensor comprises at least one ultrasonic transducer.

7. The underwater sensor assembly of claim 1, wherein the at least one first sensor comprises a plurality of sensors, and wherein the plurality of sensors are located at different distances from the bottom of the body of water when the frame sits on the bottom of the body of water.

8. The underwater sensor assembly of claim 1, wherein the at least one first sensor comprises a plurality of sensors, and wherein the plurality of sensors are located at a same distance from the bottom of the body of water when the frame sits on the bottom of the body of water.

9. An underwater sensor assembly, comprising:
a frame configured to sit on a bottom of a body of water;
at least one first sensor connected to the frame, wherein the at least one first sensor is configured to measure at least one parameter related to the body of water;
at least one cable attached at a first end to the frame and extending toward a surface of the body of water; and
at least one second sensor connected to the at least one cable between the frame and the surface of the body of water.

10. The underwater sensor assembly of claim 9, wherein the at least one second sensor is configured to measure at least one of temperature, conductivity, depth, pH, turbidity, dissolved oxygen saturation, and dissolved oxygen.

11. The underwater sensor assembly of claim 9, wherein the at least one second sensor comprises a plurality of second sensors connected to the at least one cable between the frame and the surface of the body of water, and wherein the plurality of second sensors are spaced apart from each other along the cable between the frame and the surface of the body of water.

12. The underwater sensor assembly of claim 11, wherein two or more sensors of the plurality of second sensors are configured to measure a same parameter, and wherein the two or more sensors of the plurality of second sensors measure the same parameter at different depths in the body of water.

13. The underwater sensor assembly of claim 9, wherein the at least one cable is attached at a second end to at least one buoy at the surface of the body of the water.

14. The underwater sensor assembly of claim 13, wherein the at least one cable comprises at least one data line configured to carry data from the at least one first sensor to control circuitry on the at least one buoy.

15. The underwater sensor assembly of claim 14, wherein the at least one buoy comprises a transmitter in communication with the control circuitry and configured to wirelessly transmit the data to at least one computer located outside the body of water.

16. The underwater sensor assembly of claim 15, wherein the control circuitry is configured to determine a level of sediment at the bottom of the body of water based on the distance from the at least one first sensor to the bottom of the body of water.

17. An underwater sensor assembly, comprising:
a frame configured to sit on a bottom of a body of water;
at least one first sensor connected to the frame, wherein the at least one first sensor is configured to measure at least one parameter related to the body of water;
at least one cable attached at a first end to the frame and extending toward a surface of the body of water,
wherein the at least one cable is attached at a second end to at least one buoy at the surface of the body of the water,
wherein the at least one cable comprises at least one data line configured to carry data from the at least one first sensor to control circuitry on the at least one buoy,
wherein the at least one buoy comprises a transmitter in communication with the control circuitry and configured to wirelessly transmit the data to at least one computer located outside the body of water,
wherein the control circuitry is configured to determine a level of sediment at the bottom of the body of water based on the distance from the at least one first sensor to the bottom of the body of water, and
wherein the control circuitry is configured to transmit an alert to the at least one computer when the level of sediment violates a threshold level.

18. An underwater sensor assembly, comprising:
a frame configured to sit on a bottom of a body of water; and
at least one first sensor connected to the frame, wherein the at least one first sensor is configured to measure at least one parameter related to the body of water; and
at least one cable attached at a first end to the frame and extending toward a surface of the body of water,
wherein the at least one cable is attached at a second end to at least one buoy at the surface of the body of the water,
wherein the at least one buoy comprises at least one other sensor configured to measure at least one weather related parameter, at least one air quality parameter, at least one wave related parameter, or any combination thereof.

19. An underwater sensor assembly, comprising:
a frame configured to sit on a bottom of a body of water; and
at least one first sensor connected to the frame, wherein the at least one first sensor is configured to measure at least one parameter related to the body of water,
wherein the frame comprises a simple polygonal shape with a leg extending from each corner of the simple polygonal shaped frame.

20. The underwater sensor assembly of claim 19, wherein each of the legs extends from the simple polygonal shaped frame in a direction away from the interior of the simple polygonal shaped frame.

21. A system for environmental monitoring, comprising:
an underwater sensor assembly including:
a frame configured to sit on a bottom of a body of water, and at least one first sensor connected to the frame, wherein the at least one first sensor is configured to measure at least one parameter below the surface of the body of water;

at least one buoy at a surface of the body of water; and at least one cable attached at a first end to the frame and attached at a second end opposite the first end to the at least one buoy, wherein the at least one buoy comprises at least one second sensor configured to measure at least one parameter above the surface of the body of water.

22. The system of claim 21, further comprising:

at least one third sensor connected to the at least one cable between the frame and the surface of the body of water.

* * * * *